United States Patent
Yang et al.

(12)

(10) Patent No.: US 9,580,373 B2
(45) Date of Patent: Feb. 28, 2017

(54) EXTRACTION AND PURIFICATION OF URUSHIOL FROM BOTANICAL SOURCES

(71) Applicant: Rowan University, Glassboro, NJ (US)

(72) Inventors: Catherine F. Yang, Glassboro, NJ (US); Weixing Li, Glassboro, NJ (US); Ryan Elliot, Glassboro, NJ (US); Nikita Iltchenko, Glassboro, NJ (US)

(73) Assignee: Rowan University, Glassboro, NJ (US)

( * ) Notice: Subject to any disclaimer, the term of this patent is extended or adjusted under 35 U.S.C. 154(b) by 0 days.

(21) Appl. No.: 14/646,198

(22) PCT Filed: Nov. 21, 2013

(86) PCT No.: PCT/US2013/071355
§ 371 (c)(1),
(2) Date: May 20, 2015

(87) PCT Pub. No.: WO2014/081988
PCT Pub. Date: May 30, 2014

(65) Prior Publication Data
US 2015/0284308 A1    Oct. 8, 2015

Related U.S. Application Data

(60) Provisional application No. 61/729,081, filed on Nov. 21, 2012.

(51) Int. Cl.
*C07C 35/14* (2006.01)
*B01D 11/02* (2006.01)
*A61K 36/22* (2006.01)

(52) U.S. Cl.
CPC ............. *C07C 35/14* (2013.01); *A61K 36/22* (2013.01); *B01D 11/02* (2013.01); *B01D 11/0288* (2013.01); *A61K 2236/00* (2013.01)

(58) Field of Classification Search
CPC ...................................................... C07C 35/14
See application file for complete search history.

(56) References Cited

U.S. PATENT DOCUMENTS 3,819,726 A    6/1974   Khurana et al.
7,629,006 B2 *  12/2009  Chol ...................... A61K 36/22
                                                        424/725

OTHER PUBLICATIONS

Gartner, Barbara L., et al., Seasonal Variation of Urushiol Content in Poison Oak Leaves, "American Journal of Contact Dermatitis", Mar. 1993, vol. 4, No. 1, pp. 33-36.
Ki Tae Suk et al., In vitro Antibacterial and Morphological Effects of the Urushiol Component of the Sap of the Korean lacquer tree (Rhus vernicifera Stokes) on Helicobacter pylori J. Korean Med Sci. 2010; pp. 399-404.

* cited by examiner

*Primary Examiner* — Brian J Davis
(74) *Attorney, Agent, or Firm* — Fox Rothschild LLP (57) ABSTRACT

The disclosure relates to methods for preparing urushiol from plants including, for example, poison ivy or poison oak. The methods include extraction of plant material using a primary organic solvent more polar than ethanol, followed by a solvent extraction using substantially immiscible solvents having substantially different polarities, such as hexane and acetonitrile. The method can include further purification, such as by fractionation of solvent-extracted materials using a thiazole-derivatized silica gel chromatography medium. The extracts thus generated can exhibit greater purity, higher concentration, and greater stability than extracts made using previously-known methods. The extracts can be particularly suitable for use in immunotherapeutic methods, such as desensitizing individuals who normally develop allergic contact dermatitis attributable to poison ivy or poison oak.

15 Claims, 6 Drawing Sheets

EXTRACTION AND PURIFICATION OF URUSHIOL FROM BOTANICAL SOURCES

CROSS REFERENCE TO RELATED APPLICATIONS

This application is the U.S. National Phase filing of PCT International Application No. PCT/US13/71355, filed Nov. 21, 2013, which claims priority to U.S. Provisional Application No. 61/729,081, filed Nov. 21, 2012. The contents of the foregoing applications are incorporated herein by reference in their entireties.

BACKGROUND OF THE DISCLOSURE

The disclosure relates generally to the field of immunology and allergic reactions.

Poison ivy is one of the most medically problematic plants, and is responsible for causing allergic contact dermatitis in humans. It has been estimated that approximately 85% of the US population is sensitized to these plants. While the chemistry of the allergen and the immunologic mechanism of the reaction are different, both clinical experience and animal studies suggest that poison ivy, like respiratory allergy to ragweed, should be responsive to injection immunotherapy. Ragweed allergen was identified and quantitated in the 1960's and its safe and effective immunotherapy doses identified in dose ranging studies in the 1960's and '70's. Immunotherapy has the prospective ability to lessen the abnormal immunological responses to an allergen. Double blind immunotherapy discontinuation studies of ragweed have shown that even after a full year patients show no symptoms of response to the plant. There are no known studies to validate human injection immunotherapy or identify safe and effective treatment doses and schedules for poison ivy allergies.

Urushiol is an oily organic allergen found in plants in the family Anacardiaceae. Notable plants includes cashew (in the type genus *Anacardium*), mango, pistachio, poison ivy (e.g., *Toxicodendron radicans*), poison oak (e.g., *Toxicodendron diversilobum* and *Toxicodendron pubescens*), sumac, smoke tree, marula, yellow mombin, and cuachalalate. It has been demonstrated that the heteroolefinic components of the urushiols contained in the plants within this family are not identical in structure or composition. The term urushiol as used herein includes mixtures of heteroolefinic catechols of Anacardiaceae plants, e. g., poison ivy, poison oak, cashew, pistachio, or mango, as well as to individual components of such mixtures.

Urushiol is a mixture 3-n-alk-(en)-yl catechols with varying degrees of unsaturation on either the $C_{15}$ side chain (derived from poison ivy chain) or $C_{17}$ side chain (derived from poison oak), often including those shown in FIG. 1. Conclusive identification of the structure was first made in 1934; purification yielded a yellow oil with a boiling point of 210 degrees Celsius. Urushiol primarily resides in resin canals, present in the leaves, flowers, roots, bark and fruits of the plant. In addition to poison oak, poison ivy, and poison sumac, other urushiol-containing plants in this family are the Chinese and Japanese lac trees (*R. verniciflua* L.) and the Yunnan, Formosan and Indo-Chinese lac trees (*R. succedanea* L.). Agriculturally significant Mango (*M. indica*), Cashew (*A. occidentale*), and Pistachio (*P. vera*) trees also contain urushiol.

The long aliphatic side chains of these catechols cause the molecules to be hydrophobic, making urushiol one of the most lipophilic haptens that cause contact dermatitis. As a result of this lipophilicity urushiol tends to concentrate in cellular membranes. Upon contact with human tissue, the catechol ring undergoes oxidation, forming an electrophilic o-quinone. This undergoes a regiospecific attack by model sulfhydryl and amino nucleophiles present on proteins to form the adduct. However, the lack of covalent bonding between urushiol and cell membranes used for introduction into cultures makes the mechanism of antigen presentation unclear.

In vivo experiments suggest that T-cell receptors may be directed against the side chain, with the di-saturated and tri-saturated chains producing the majority of the immunological response. Yet due to the hydrophobic nature of the molecule, the alkyl side chain should be buried within the membrane leaving the catechol ring near the surface. Therefore it is difficult to theorize how the side chain could move out of the membrane and have an effect upon immunological response. One proposed mechanism attributes it to a membrane vesicle. Alternatively T-cell reaction could be against the catechol ring, and increasing reactivity with unsaturated side chains could be due to an altered presentation of the catechol ring.

Immunotherapy with water-soluble ragweed antigen E has been shown to not only prevent reactions on natural exposure during immunotherapy but also to provide durable protection for at least a year after stopping treatment. Double blind immunotherapy discontinuation studies of ragweed have shown that, even after a full year, patients show no symptoms of response to the antigen. Based on immunological studies of ragweed, it was hypothesized that urushiol can be extracted and used in immunotherapy against contact dermatitis. However, previous extraction methods have proven difficult and inefficient, being multi-stepped and involving multiple solvents. The most common technique used by others involves soaking plant material in ethanol followed by distillation or dry packed silica column chromatography. Urushiol congeners can be separated using HPLC if desired. An example of an urushiol extraction method (hereinafter the "ElSohly method") described by ElSohly et al. (*J. Nat. Prod.,* 1982, 45(5):532-538) in summarized in FIG. 2.

The ElSohly method and other multiple-solvent purification methods have shortfalls, including use of undesirably large quantities of solvents, restriction to small (volumetric) scale processing, and low yields. Limitations of crude ethanol extracts as allergy vaccines include limited storage stability and urushiol concentrations insufficient for effective treatment of moderately sensitive individuals.

Crude ethanol extracts having urushiol concentrations up to 1-2 milligram per milliliter have been described. (Coifman R E, "Successful immunotherapy for poison ivy," presented to 2010 Annual Meeting of the American Academy of Allergy Asthma & Immunology, New Orleans La., 28 Feb. 2010 (Abs. 142), epub J. Allerg. Clin. Immunol. 2010 (February)).

A need exists for improved methods for extraction of urushiol from plant materials at concentrations and purity levels suitable for immunotherapy or other treatment of hypersensitivity.

SUMMARY OF THE DISCLOSURE

This disclosure relates to a method for preparing a concentrated urushiol extraction of a plant, comprising soaking materials from the plant in at least one primary organic solvent selected from the group consisting of methylene chloride, isopropanol, tetrahydrofuran (THF), dichloromethane (DCM), acetonitrile, dimethoxyethane, propanol, chloroform, and pentane, or combinations of these, filtering out the plant materials forming an initial extract, removing the primary solvent from the initial extract forming a crude extract, combing the crude extract with hexane forming a resuspension, extracting the resuspension with acetonitrile forming an acetonitrile fraction and a depleted fraction, and removing acetonitrile from the acetonitrile fraction producing a concentrated urushiol extract.

The plant can be selected from the group consisting of cashews, pistachios, mangos, poison ivies, poison oaks, sumacs, smoke trees, marulas, yellow mombins, cuachalalates, lac trees, rengus tree, Burmese lacquer tree, India marking nut tree, *ginkgo biloba*, and combination of these. The materials from the plant may be leaves, stems, bark, or shells.

The materials from the plant can be shredded before soaking in the primary solvent. The soaking of materials from the plant may also including actively mixing (e.g., stirring or shaking) the materials and the primary solvent.

The extraction method or portions of it are preferably performed at or below 30 degree Celsius.

The disclosure herein also relates to a method for preparing a concentrated urushiol extraction of a plant. That method includes fractioning an urushiol preparation using a thiazole-derivatized chromatography medium, such as a thiazole-derivatized silica gel (a "thiazole silica gel"). Fractionating with thiazole silica gel involves contacting an urushiol preparation with thiazole silica gel, and eluting urushiol therefrom using chloroform (e.g., by applying to the gel a fluid having an increasing proportion of chloroform over time). The fractionating with thiazole silica gel may be performed at a sub-atmospheric pressure, such as under ordinary laboratory "vacuum" conditions.

The disclosure also relates to a highly purified urushiol extract of a plant having a purity of more than 96% (w/w). The highly pure urushiol extract may be produced and purified by the aforementioned methods.

DETAILED DESCRIPTION

The disclosure relates to methods of preparing urushiol and related compounds from botanical sources such as plants of the Anacardiaceae family, including poison ivy and poison oak. In particular, this disclosure relates to extraction of urushiol to produce a substantially purified urushiol product, including products suitable to diagnose and treat allergic contact dermatitis, such as that resulting from contact with poison ivy or poison oak, or suitable for use as a vaccine or immunotherapy agent.

Within the context of this disclosure, the term "vaccine" or "allergy vaccine" refers to a compound that can induce tolerance to undesirable cell-mediated immunity conditions, such as allergic contact dermatitis. The methods described herein can be adapted for extraction of urushiol from plants of the family Anacardiaceae and from other plants, such as cashew, pistachio, mango, Rengus tree, Burmese lacquer tree, India marking nut tree, and the shell of the cashew nut, as well as *ginkgo biloba*.

Three urushiol catechols have an unsaturated side chain and these catechols are believed to be progressively less stable than the saturated fourth component, 3-n-pentadecyl catechol, and thus more prone to polymerization and oxidation reactions as the degree of unsaturation in the side chain increases from one to three olefinic bonds. Aged samples of urushiol have variable compositions of these unsaturated components along with their polymers and oxidation products, depending upon the degree of prior exposure to air, water, and light, as well as the presence of acidic or basic conditions and elevated temperatures.

Unsaturated components of urushiol show a tendency to polymerize under acidic conditions and to oxidize under aerobic conditions, with oxidation being accelerated in an alkaline environment. These reactions lead to products of a polymeric nature and with a loss in aromaticity. For these reasons, elevated temperatures and exposure to air should be avoided during the extraction process. It is also advisable to use freshly collected raw materials when extracting urushiol from plant sources.

The methods of preparing urushiol described herein include extraction with a primary organic solvent to form an initial extract, stripping the primary solvent from the initial extract to yield a crude extract and prior to solvent extraction using a mixture of a more-polar first solvent and a less-polar second solvent that are substantially immiscible with one another under the extraction conditions used (e.g., hexane and acetonitrile used at a temperature<30 degrees Celsius).

The primary solvent should be less polar, and preferably more hydrophobic, than ethanol. However, a few relatively hydrophilic solvents (e.g., acetonitrile and tetrahydrofuran) can yield acceptable results Examples of suitably non-polar and hydrophobic solvents include methylene chloride, isopropanol, dichloromethane, dimethoxyethane, propanol, chloroform, pentane, and mixtures of these.

Figure 1:
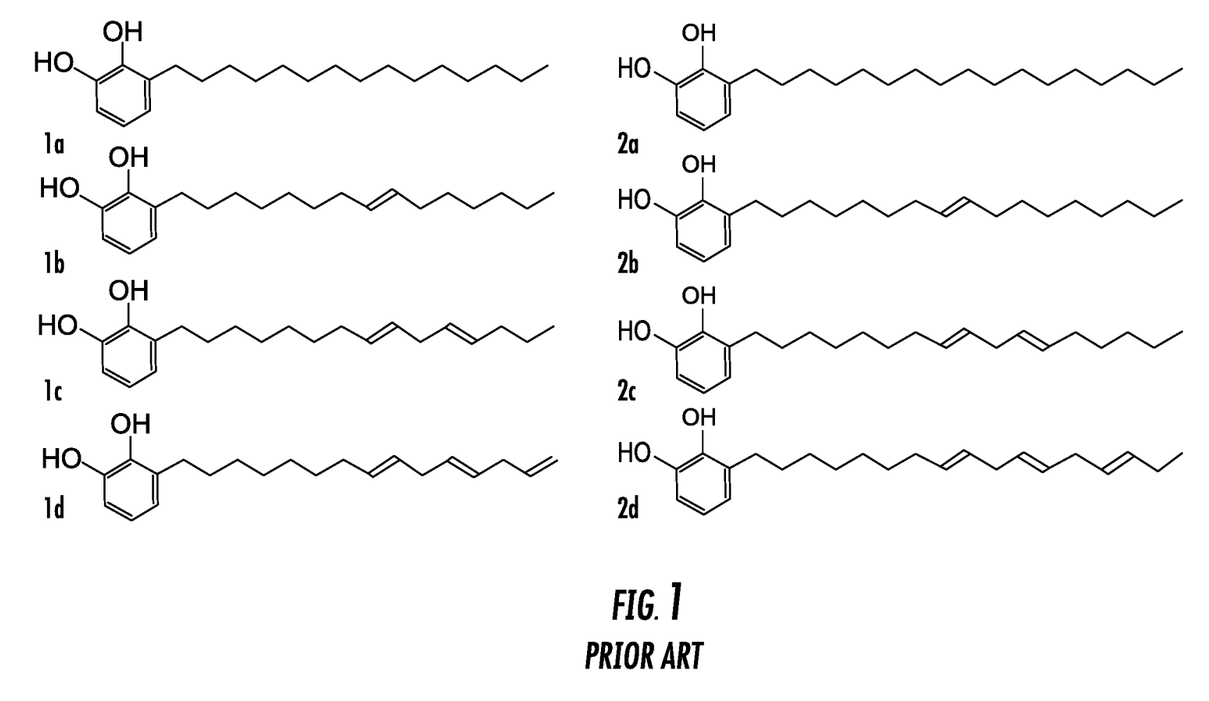
FIG. 1 is a series of chemical structures of urushiol congeners that occur in poison ivy and poison oak. Individual congeners that are shown include, for poison ivy: 1a is pentadecyl catechol (PDC), 1b is monounsaturated (8-9) PDC, 1c is diunsaturated (8-9, 11-12) PDC, and 1d is triunsubstituted (8-9, 11-12, 14-15) PDC: and for poison oak: 2a is heptadecyl catechol (HDC), 2b is monounsaturated (8-9) HDC, 2c is diunsaturated (8-9, 11-12) HDC, and 2d is triunsubstituted (8-9, 11-12, 14-15) HDC.
Figure 2:
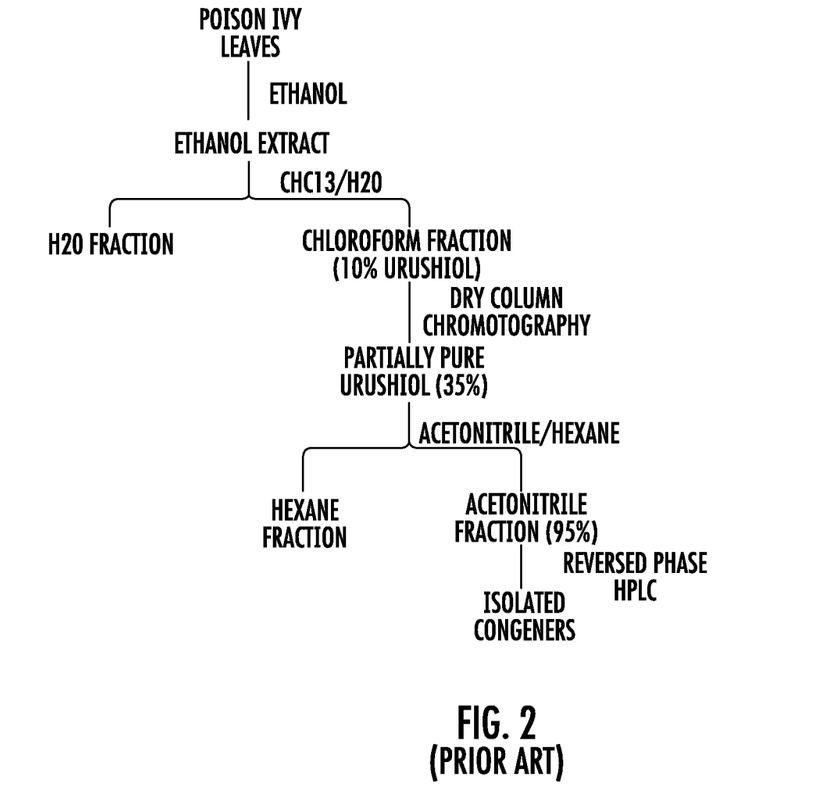
FIG. 2 illustrates a previously described method of preparing urushiol.
Figure 3:
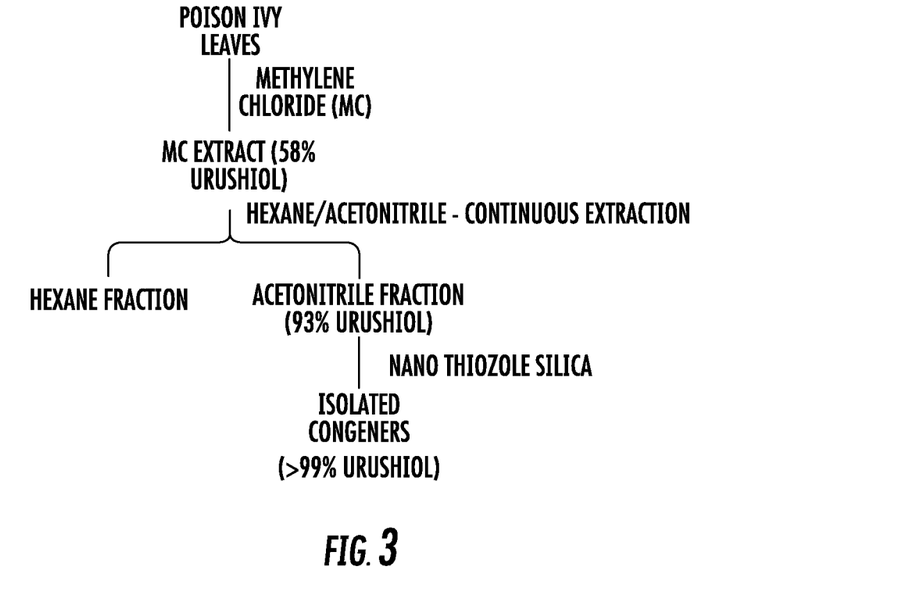
FIG. 3 illustrates a method described herein for preparing urushiol, using methylene chloride as the primary solvent.

An example of the preparative method using methylene chloride as the primary solvent is shown in FIG. 3. In that method, the primary solvent used in the initial extraction is removed by evaporation to yield the crude extract. The crude extract is resuspended in hexane (or another aliphatic hydrocarbon solvent) and acetonitrile. Because those two solvents are immiscible under the conditions used, materials in the crude extract can partition between the immiscible solvent phases. The urushiol extract from the acetonitrile fraction can then be concentrated, and acetonitrile removed by evaporation, forming a concentrated urushiol extract. The concentrated urushiol extract can then be resuspended in a suitable solvent, such as ethyl alcohol, and stored. Concentrated urushiol can be separated into congeners by means of high pressure liquid chromatography or other similar methods, if desired.

In the methods used in the examples described herein, processing steps were performed at room temperature (i.e., ca. 20 degrees Celsius). The preparative procedures are preferably performed at temperatures below 30 degree Celsius.

The ElSohly method includes multiple steps, including ethanol extraction of poison ivy leaves, followed by chloroform/water fractionation, dry-packed silica-gel column chromatography, and hexane/acetonitrile partitioning. The extraction methods disclosed herein have the advantage of utilizing a single primary solvent and fewer overall steps. Use of single solvents can avoid toxicity in humans. The methods described herein also can achieve higher yield and purity with fewer purification steps than prior methods, and improve the stability of the extraction products. The methods described herein typically provide yields of urushiol in the range of 1.33-1.43 grams per kilogram of raw material (i.e., a 0.133-0.143% (w/w) yield).

Figure 4:
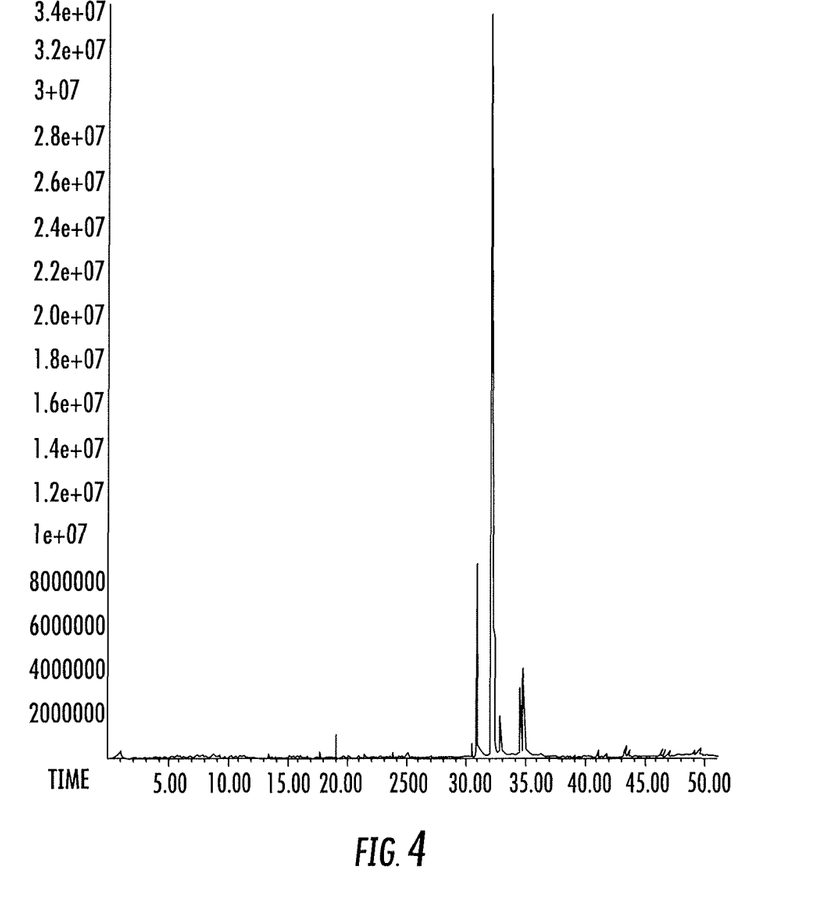
FIG. 4 is a gas chromatograph profile of a poison ivy urushiol extract prepared as described herein.

The purity of the urushiol prepared according to the method disclosed herein was higher, as determined by gas chromatography-mass spectrometric (GCMS) analysis, than the reported purity of urushiol extract using the ElSohly method. The high purity urushiol extract obtained by the methods disclosed herein is indicated by the gas chromatography profile shown in FIG. 4. Furthermore, the concentration of urushiol prepared according to the methods disclosed herein is higher than previously achievable. The ElSohly method has been demonstrated to yield an urushiol extract having a concentration not greater than about 2 milligram per milliliter. The concentration of urushiol in extracts made using the process described herein was shown to be upwards of 50 milligram per milliliter.

These improved characteristics are highly relevant to important intended uses of urushiol preparations, such as reagents for immunologic treatment of humans who experience allergic reactions upon contact with poison ivy or poison oak. Effective treatment depends heavily upon the sensitivity of the individual seeking treatment and the concentration and purity of urushiol concentrations that are available for treatment. As the individual's sensitivity to urushiol decreases, more urushiol is needed to elicit a desired degree of reaction and a higher dose of urushiol extract is needed to achieve successful immunotherapy treatment. A higher dose must come from a higher concentration of urushiol in the extract, and not from simply increasing the volume of the urushiol extract, because there are physiological limits to the quantity of reagent that can be effectively delivered to a patient. It is therefore preferable to use immunotherapy agents having high urushiol concentration and low solvent content.

The high concentration urushiol that can be prepared using the methods described herein facilitate immunological treatment of people who exhibit moderate or low sensitivity to poison ivy or poison oak. The urushiol preparation obtained using the methods described herein permits a much higher amount of urushiol to be practically applied in order to elicit an allergic response in these patients.

The urushiol extract prepared as described herein can be further purified by chromatography, if desired. A preferred chromatographic method is liquid chromatography employing a bed packed with a thiazole-derivatized medium, such as the thiazole silica gel described in the examples herein. Thiazole silica gel can be prepared by reacting a silica gel by reacting with a thiazole compound, for example, 5-(4-(trimethoxysilyl)butyl)thiazole. The thiazole silica gel may be dry-packed in a column using known methods. An urushiol sample can be applied to the dry-packed thiazole silica column and eluted therefrom by passing over the column packing a solvent that includes a solvent (e.g., chloroform) that will displace urushiol from the thiazole-derivatized medium. The chloroform or other solvent can thereafter be removed by evaporation. If necessary or desired, trace amount of chloroform or other solvent can be removed by ether distillation.

Compared to the unmodified silica gel used in the ElSohly method, thiazole-modified silica gel enhances purification efficiency. Urushiol extract can be purified using thiazole silica gel chromatography to a purity greater than 96% by weight (ignoring solvent) or higher, for example, above 97%, above 98%, or above 99%.

Table 1 summarizes examples of urushiol preparations from poison ivy leaves that were performed as described herein. Examples 2-10 illustrate the methods described in this disclosure and generally exhibited higher yield and greater urushiol concentration than the ElSohly method.

Comparison of gas chromatography peak distributions and relative abundances the effect of varying extraction routes on relative congener/isomer concentrations, as shown in Table 2. Relative congener concentration can also vary with the identity and treatment of plant raw materials used in the extraction (for example, the plant age, the season or time of year collected, and the plants' specific growth conditions). In all performed extraction routes the monounsaturated urushiol was in highest concentration (~43%), averages of percentage concentration varying statistically insignificantly among different extractions but having a relatively high standard deviation within each data set (as high as ±11% for pentane extractions) (Table 2). The next most prominent congener (11-25%) was the di-unsaturated urushiol which varied among the different extractions (Table 2). The fully saturated congener, was present in less concentration (5-6%) without variation among reactions (Table 2). The final urushiol congener, the thrice disaturated molecule was present in nearly undetectable levels throughout all extracts (1-3%) (Table 2). Ethoxy derivatives of urushiol as well as E/Z isomers varied significantly among extractions suggesting their levels are greatly dependent on the technique and care used during the purification, as well as age and other factors.

TABLE 1

Summary of Examples of Poison Ivy Urushiol Extraction and Purification

| Example | Primary Solvent | Total Steps | Poison Ivy Leaf Weight (g) | Crude Purity (wt %) | Acetonitrile Fraction Purity (wt %) | Weight (g) | Final Purity (wt %) |
|---|---|---|---|---|---|---|---|
| 1 | Ethanol | 5 | 30 | 42 | ~42 | 0.25 | 90 |
| 2 | Methylene Chloride | 3 | 90 | 58 | 58 | 0.62 | 99.5 |
| 3 | Isopropanol/THF | 3 | 30 | 32 | 92 | 0.35 | 98 |
| 4 | DCM/THF | 3 | 29 | 30 | 90 | 0.30 | N/A |
| 5 | THF | 3 | 35 | 35 | 93 | 0.36 | 97.5 |

TABLE 1-continued Summary of Examples of Poison Ivy Urushiol Extraction and Purification

| Example | Primary Solvent | Total Steps | Poison Ivy Leaf Weight (g) | Crude Purity (wt %) | Acetonitrile Fraction Purity (wt %) | Weight (g) | Final Purity (wt %) |
|---|---|---|---|---|---|---|---|
| 6 | Acetonitrile | 3 | 32 | 34 | 93 | 0.31 | 96.5 |
| 7 | Dimethoxyethane | 3 | 60 | 34 | 93 | 0.62 | 98.5 |
| 8 | Propanol | 3 | 60 | 34 | 93 | 0.60 | 97.5 |
| 9 | Chloroform | 3 | 35 | 67 | 90 | 0.58 | 94.5 |
| 10 | Pentane | 3 | 40 | 42 | 86 | 0.39 | 91.5 |

TABLE 2

Peak analysis of gas chromatographs of average purified methylene chloride, chloroform and pentane extracts shown with standard deviation.

| Peak | Urushiol Congener | Pentane (%) | Chloroform (%) | Methylene Chloride (%) |
|---|---|---|---|---|
| 1 | 1d | 1.5 ± 0.9 | 2.7 ± 0.6 | 2.7 ± 0.9 |
| 2 | 1c | 43 ± 11 | 43 ± 8.7 | 44 ± 4.0 |
| 3 | 1b | 15 ± 2.9 | 25 ± 5.4 | 12 ± 3.8 |
| 4 | 1a | 6.1 ± 1.1 | 6.5 ± 1.4 | 5.3 ± 0.9 |
| 5 | 1a | 1.9 | 1.5 ± 0.1 | 2.1 ± 0.1 |
| 6 | 1c | 3.3 ± 2.2 | 1.9 ± 1.2 | 3.2 ± 4.0 |
| 7 | 2c | 1.5 ± 0.4 | 2.2 ± 1.6 | 3.0 ± 1.0 |
| 8 | 2b | 4.3 ± 3.2 | 5.5 ± 4.0 | 11 ± 6 |
| 9 | 2a | 6.5 ± 1.8 | 3.1 ± 0.7 | 9.2 ± 5.4 |

Figure 5:
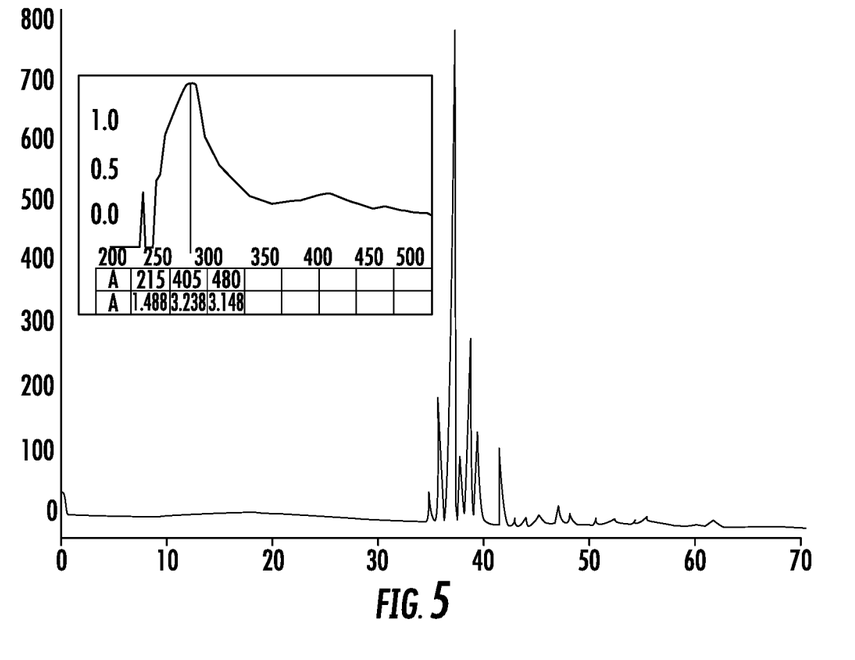
FIG. 5 is a graph that illustrates stability over time of a poison ivy urushiol extract prepared as described herein.
Figure 6:
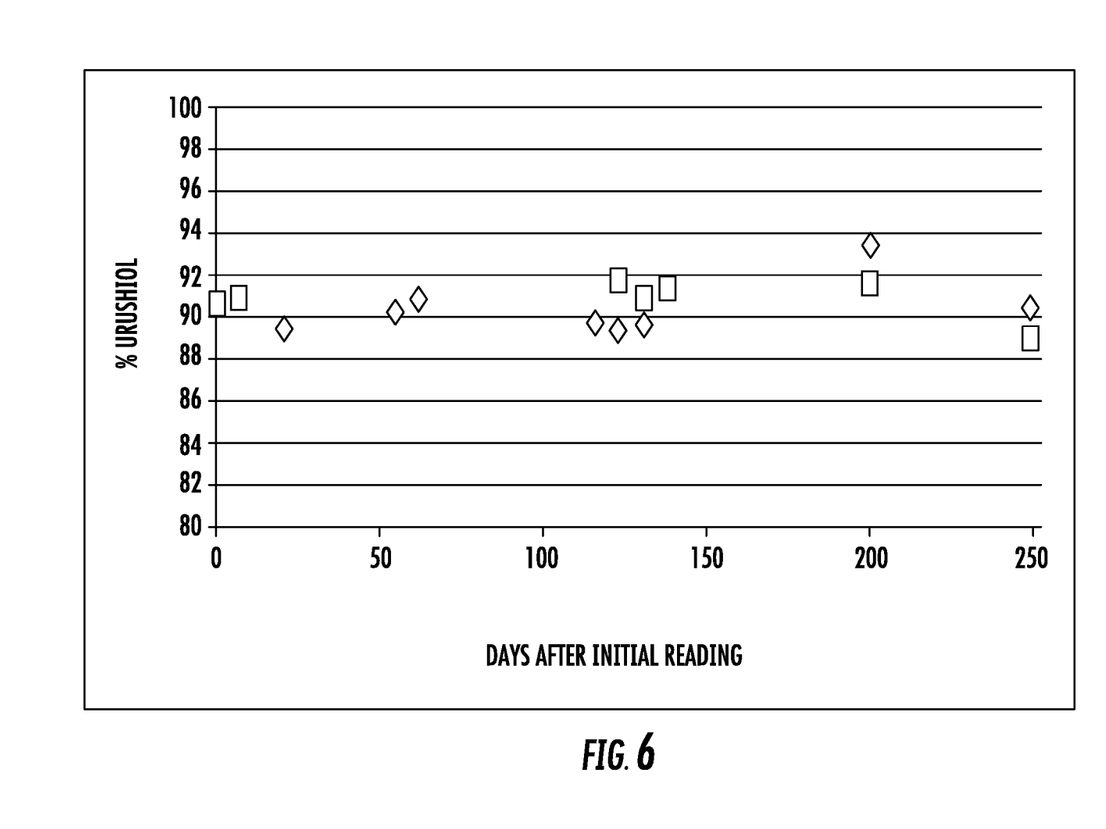
FIG. 6 is a depiction of % urushiol, wherein Diamonds represent samples stored at 3 degrees Celsius, and Rectangles represent samples stored at 23 degrees Celsius.

Urushiol in preparations made as described herein have shown remarkable stability. Urushiol is stable at a concentration of 50 milligram per milliliter in ethanol. FIG. 5 shows the stability of an urushiol extract prepared using methylene chloride as the primary solvent. Samples were tested up to 250 days stored at 3 degrees Celsius (Diamonds) and 23 degrees Celsius (Squares). No significant difference was observed over the time period for either set of stored samples.

Using high concentration urushiol preparations made as described herein, vaccines can be prepared that are suitable to induce tolerance in patients with significant clinical disease, but with relatively low levels of pre-treatment patch-test sensitivity. Both clinical tolerance to natural exposure and reduction in patch test sensitivity have lasted nine months or more using such vaccines. These vaccines are believed to be the first to induce long-lasting tolerance to urushiol in previously sensitized humans.

The subject matter of this disclosure is now described with reference to the following Examples. The Examples are provided for the purpose of illustration only, and the subject matter is not limited to these Examples, but rather encompasses all variations which are evident as a result of the teaching provided herein.

The methods described herein are illustrated in the following example. While the example involves the preparation of urushiol from poison ivy, an essentially similar procedure is followed in preparing urushiol from poison oak or from other urushiol-bearing plants.

Plant Material

Poison ivy (*Toxicodendron radicans*) leaves were collected in June, July and August 2011 in a forest located in Mantua, N.J. The leaves were stored in a refrigerator substantially immediately after harvest and used for extraction within 7-10 days. Freshly collected poison ivy raw material (leaves and stems) was torn by hand only to the extent that each leaf was torn at least once before solvent extraction. It is expected that more thorough shredding of such materials will enhance extraction yield.

EXAMPLE 1

Poison ivy leaves (30 grams) were soaked in 100% ethanol (200 milliliters) for approximately 4 hours at room temperature. The resulting solution was filtered to remove the leaves, collected in a round bottom flask, and stripped of solvent on a rotary evaporator. GCMS analysis showed approximately 42% w/w urushiol. The resulting dark green residue was then resuspended in 100 milliliters chloroform and washed thrice with water. The organic fractions were dried over sodium sulfate (10 gram) to remove traces of water. The solvent was removed on a rotary evaporator with temperature between 20 and 30 degrees Celsius to yield a residue. That residue was fractionated by column chromatography (15 centimeter length by 4 centimeter diameter) with dry packed silica gel under laboratory vacuum and eluted with chloroform. Fractions were collected based on color and tested for urushiol presence by a ferric chloride test and GCMS.

Fractions that tested positive for catechol were combined, stripped of solvent, and resuspended in 100 milliliters hexane. The resuspended material was thrice extracted with 100 milliliter aliquots of acetonitrile. The acetonitrile aliquots were combined and evaporated, yielding 0.25 gram of dark green oil. GCMS analysis showed 90% w/w urushiol. The concentrated extract was resuspended in ethanol and stored in refrigerator (3 degrees Celsius) in order to slow the degradation process.

EXAMPLE 2

Poison ivy leaves and stems (90 grams) were soaked in methylene chloride (800 milliliters) for 4.5 hours at room temperature. The solution was filtered and stripped of solvent. GCMS analysis showed 58% w/w urushiol. The resulting dark brown oil (0.997 g) was resuspended in ethanol (100 milliliters) and dried over sodium sulfate (10 gram). The solution was then split into 3 equal volumes and each fraction was stripped of solvent. Dark brown oil (0.332 g) was resuspended in 100 milliliters hexane and extracted with acetonitrile (100 milliliters) in a Soxhlet continuous extraction apparatus. Acetonitrile fractions were collected and the solvent was evaporated to yield a green-brown oil (0.62 gram). GCMS analysis, showed 93% w/w urushiol.

Further purification was achieved by column chromatography (15 centimeter length by 4 centimeter diameter) with dry packed thiazole silica gel eluted with chloroform under laboratory vacuum. The purity was 99.5%. The solution was resuspended in ethanol and placed in sealed amber vials under refrigeration (3 degrees Celsius) to be formulated for clinical use.

EXAMPLE 3

Poison ivy leaves (30 grams) were soaked in 1:1 isopropanol:THF (200 milliliters) for approximately 4 hours at room temperature. The resulting solution was filtered to remove the leaves, collected in a round bottom flask, and stripped of solvent using a rotary evaporator. GCMS analysis showed approximately 32% w/w urushiol. The resulting dark green residue was resuspended in 100 milliliters chloroform and washed thrice with water. The organic fractions were dried over sodium sulfate (10 gram) to remove traces of water. The solvent was removed on a rotary evaporator at a temperature between 20 and 30 degree Celsius to yield a residue. The residue was fractionated by column chromatography (15 centimeter length by 4 centimeter diameter) using a dry packed silica gel medium under laboratory vacuum and fractions were eluted with chloroform. Fractions were collected based on color and tested for urushiol presence by a ferric chloride test and GCMS.

Fractions that tested positive for catechol were combined, stripped of solvent, and resuspended in 100 milliliters hexane and solvent extraction using 100 milliliters acetonitrile and a continuous extraction device. Acetonitrile fractions were combined and the solvent was evaporated therefrom, yielding 0.35 gram of dark green oil. GCMS analysis showed 92% w/w urushiol. Further purification was achieved by column chromatography (15 centimeter length by 4 centimeter diameter) using a dry packed thiazole silica gel medium under laboratory vacuum. The purity was 98%. The concentrated extract was resuspended in ethanol and stored in a refrigerator (3 degrees Celsius) in order to slow degradation.

EXAMPLE 4

Poison ivy leaves (29 grams) were soaked in 1:1 dichloromethane: THF (200 milliliters) for approximately 4 hours at room temperature. The resulting solution was filtered to remove the leaves, collected in a round bottom flask, and stripped of solvent using a rotary evaporator. GCMS analysis showed approximately 30% w/w urushiol. The resulting dark green residue was resuspended in 100 milliliters chloroform and extracted thrice with water using a continuous extraction device. The organic fractions were dried over sodium sulfate (10 gram) to remove traces of water. The solvent was removed using a rotary evaporator at a temperature between 20 and 30 degree Celsius to yield a residue. The residue was fractionated by column chromatography (15 centimeter length by 4 centimeter diameter) using a dry packed silica gel medium under laboratory vacuum and fractions were eluted with chloroform. Fractions were collected based on color and tested for urushiol presence by a ferric chloride test and GCMS.

Fractions that tested positive for catechol were combined, stripped of solvent, and resuspended in 100 milliliters hexane followed by three rounds of solvent extraction, each round involving extraction with 100 milliliters of acetonitrile. The acetonitrile aliquots were combined and acetonitrile was evaporated therefrom, yielding 0.30 gram of dark green oil. GCMS analysis showed 90% w/w urushiol. The concentrated extract was resuspended in ethanol and stored in a refrigerator.

EXAMPLE 5

Poison ivy leaves (35 grams) were soaked in THF (200 milliliters) for approximately 4 hours at room temperature. The resulting solution was filtered to remove the leaves, collected in a round bottom flask, and stripped of solvent using a rotary evaporator. GCMS analysis showed approximately 31% w/w urushiol. The resulting dark green residue was resuspended in 100 milliliters chloroform and washed thrice with water. The organic fractions were dried over sodium sulfate (10 gram) to remove traces of water. The solvent was removed using a rotary evaporator at a temperature between 20 and 30 degree Celsius to yield a residue. The residue was fractionated by column chromatography (15 centimeter length by 4 centimeter diameter) using a dry packed silica gel medium under laboratory vacuum, and fractions were eluted with chloroform. Fractions were collected based on color and tested for urushiol presence by a ferric chloride test and GCMS.

Fractions that tested positive for catechol were combined, stripped of solvent, and resuspended in 100 milliliters hexane. The resuspended material was extracted using 100 milliliters of acetonitrile in a continuous extraction device. Acetonitrile fractions were combined and acetonitrile was evaporated therefrom, yielding 0.36 gram of dark green oil. GCMS analysis showed 93% w/w urushiol. Further purification was achieved by column chromatography (15 centimeter length by 4 centimeter diameter) using a dry packed thiazole silica medium, and fractions were eluted with chloroform under laboratory vacuum. The purity was 97.5%. The concentrated extract was resuspended in ethanol and stored in a refrigerator.

EXAMPLE 6

Poison ivy leaves (32 grams) were soaked in acetonitrile (200 milliliters) for approximately 4 hours at room temperature. The resulting solution was filtered to remove the leaves, collected in a round bottom flask, and stripped of solvent using a rotary evaporator. GCMS analysis showed approximately 34% w/w urushiol. The resulting dark green residue was resuspended in 100 milliliters chloroform and washed thrice with water using a continuous extraction device. The organic fractions were dried over sodium sulfate (10 gram) to remove traces of water. The solvent was removed using a rotary evaporator at temperature between 20 and 30 degree Celsius to yield a residue. The residue was fractionated by column chromatography (15 centimeter length by 4 centimeter diameter) using a dry packed silica gel medium with laboratory vacuum applied, and fractions were eluted with chloroform. Fractions were collected based on color and tested for urushiol presence by a ferric chloride test and GCMS.

Fractions that tested positive for catechol were combined, stripped of solvent, and resuspended in 100 milliliters hexane. The resuspended material was extracted using 100 milliliters of acetonitrile in a continuous extraction device. Acetonitrile fractions were combined and acetonitrile was evaporated therefrom, yielding 0.31 gram of dark green oil. GCMS analysis showed 93% w/w urushiol. Further purification was achieved by column chromatography (15 centimeter length by 4 centimeter diameter) using a dry packed thiazole silica gel medium, and fractions were eluted with chloroform under vacuum. The purity was 96.5%. The concentrated extract was resuspended in ethanol and stored in a refrigerator

EXAMPLE 7

Poison ivy leaves (60 grams) were soaked in dimethoxyethane (400 milliliters) for approximately 4 hours at room temperature. The resulting solution was filtered to remove the leaves, collected in a round bottom flask, and stripped of solvent using a rotary evaporator. GCMS analysis showed approximately 34% w/w urushiol. The resulting dark green residue was then resuspended in 100 milliliters ether and washed thrice with water. The organic fractions were dried over sodium sulfate (20 gram) to remove traces of water. The solvent was removed using a rotary evaporator at a temperature between 20 and 30 degrees Celsius to yield a residue. The residue was purified by column chromatography (25 centimeter length by 4 centimeter diameter) using a dry packed silica gel medium with laboratory vacuum applied, and fractions were eluted with chloroform. Fractions were collected based on color and tested for urushiol presence by a ferric chloride test and GCMS.

Fractions that tested positive for catechol were combined, stripped of solvent, and resuspended in 200 milliliters hexane. The resuspended material was extracted using 100 milliliters of acetonitrile in a continuous extraction device. Acetonitrile fractions were combined and acetonitrile was evaporated therefrom, yielding 0.62 gram of dark green oil. GCMS analysis showed 93% w/w urushiol. Further purification was achieved by column chromatography (15 centimeter length by 4 centimeter diameter) using a dry packed thiazole silica medium, and fractions were eluted with chloroform under laboratory vacuum. The purity was 98.5%. The concentrated extract was resuspended in ethanol and stored in a refrigerator.

EXAMPLE 8

Poison ivy leaves (60 grams) were soaked in propanol (400 milliliters) for approximately 4 hours at room temperature. The resulting solution was filtered to remove the leaves, collected in a round bottom flask, and stripped of solvent using a rotary evaporator. GCMS analysis showed approximately 34% w/w urushiol. The resulting dark green residue was resuspended in 100 milliliters ether and washed thrice with water. The organic fractions were dried over sodium sulfate (20 gram) to remove traces of water. The solvent was removed using a rotary evaporator at a temperature between 20 and 30 degrees Celsius to yield a residue. The residue was fractionated by column chromatography (25 centimeter length by 4 centimeter diameter) using a dry packed silica gel medium with laboratory vacuum applied, and fractions were eluted with chloroform. Fractions were collected based on color and tested for urushiol presence by a ferric chloride test and GCMS.

Fractions that tested positive for catechol were combined, stripped of solvent, and resuspended in 200 milliliters hexane. The resuspended material was extracted with 100 milliliters of acetonitrile using a continuous extraction device. Acetonitrile fractions were combined and acetonitrile was evaporated therefrom, yielding 0.60 gram of dark green oil. GCMS analysis showed 93% w/w urushiol. Further purification was achieved by column chromatography (15 centimeter length by 4 centimeter diameter) using a dry packed thiazole silica gel medium, and fractions were eluted with chloroform under laboratory vacuum. The purity was 97.5%. Concentrated extract was resuspended in ethanol and stored in a refrigerator.

EXAMPLE 9

Poison ivy leaves (35 grams) were soaked in 150 milliliters of chloroform for approximately 4 hours at room temperature. The resulting solution was filtered to remove the leaves, collected in a round bottom flask, and stripped of solvent using a rotary evaporator. GCMS analysis showed approximately 30% w/w urushiol. The resulting dark green residue was resuspended in 100 milliliters chloroform and washed thrice with water using a continuous extraction device. The organic fractions were dried over sodium sulfate (10 gram) to remove traces of water. The solvent was removed using a rotary evaporator at a temperature between 20 and 30 degrees Celsius to yield a residue. The residue was fractionated by column chromatography (15 centimeter length by 4 centimeter diameter) using a dry packed silica gel medium under laboratory vacuum, and fractions were eluted with chloroform. Fractions were collected based on color and tested for urushiol presence by a ferric chloride test and GCMS.

Fractions that tested positive for catechol were combined, stripped of solvent, and resuspended in 200 milliliters hexane. The resuspended material was extracted with 100 milliliters of acetonitrile in a continuous extraction device. Acetonitrile fractions were combined and acetonitrile was evaporated therefrom, yielding 0.55 gram of dark green oil. GCMS analysis showed 91% w/w urushiol. Further purification was achieved by column chromatography (15 centimeter length by 4 centimeter diameter) using a dry packed thiazole silica gel medium, and fractions eluted with chloroform under laboratory vacuum. The purity was 94.5%. Concentrated extract was resuspended in ethanol and stored in a refrigerator.

EXAMPLE 10

Poison ivy leaves (40 grams) were soaked in 200 milliliters of pentane for approximately 4 hours at room temperature. The resulting solution was filtered to remove the leaves, collected in a round bottom flask, and stripped of solvent on a rotary evaporator. GCMS analysis showed approximately 42.4% w/w urushiol. The resulting dark green residue was resuspended in 100 milliliters chloroform and washed thrice with water using a continuous extraction process. The organic fractions were dried over sodium sulfate (10 gram) to remove traces of water. The solvent was removed using a rotary evaporator at a temperature between 20 and 30 degrees Celsius to afford a residue. The residue was fractionated by column chromatography (15 centimeter length by 4 centimeter diameter) using a dry packed silica gel medium with laboratory vacuum applied, and fractions were eluted with chloroform. Fractions were collected based on color and tested for urushiol presence by a ferric chloride test and GCMS.

Fractions that tested positive for catechol were combined, stripped of solvent, and resuspended in 200 milliliters hexane. The resuspended material was extracted with 100 milliliters acetonitrile using a continuous extraction device. Acetonitrile fractions were combined and acetonitrile was evaporated therefrom, yielding 0.50 gram of dark green oil. GCMS analysis showed 86.5% w/w urushiol. Further purification was achieved by column chromatography (15 centimeter length by 4 centimeter diameter) using a dry packed thiazole silica gel medium, and fractions were eluted with chloroform under laboratory vacuum. The purity was 91.5%. Concentrated extract was resuspended in ethanol and stored in a refrigerator.

EXAMPLE 11

Silica (25 grams) was suspended in 200 milliliters of dry toluene before adding 10 milliliters of 3-aminopropyltriethoxysilane. The mixture was stirred and refluxed for 24 hours under a nitrogen atmosphere. The resulting product was filtered and washed twice with 50 milliliters of toluene, twice with 50 milliliters of ethanol, and four times with 50 milliliters of dichloromethane. The product was dried for 6 hours at room temperature under laboratory vacuum, and then immersed in 200 milliliters of toluene prior to adding 6.25 milliliters of ethyl-2-bromopropionate. The mixture was again stirred and refluxed for 24 hours under a nitrogen atmosphere. The resulting product was filtered and washed twice with 50 milliliters of toluene, four times with 50 milliliters of ethanol, and four times with 50 milliliters of dichloromethane. The resulting product was dried for 6 hours at room temperature under laboratory vacuum, dispersed in 200 milliliters of dry acetonitrile, and then 8.3 grams of 2-(thiazol-4-yl)ethanamine was added. The mixture was stirred and refluxed for 24 hours under a nitrogen atmosphere. The product was filtered and washed twice with 50 milliliters of acetonitrile, six times with 50 milliliters of ethanol, and four times with 50 milliliters of dichloromethane. This final product was dried at room temperature under vacuum to yield a thiazole silica gel.

EXAMPLE 12

Urushiol congeners were separated as follows. An absorbance spectrum was obtained using purified extract showing maximum absorbance at 276 nanometers. High pressure liquid chromatography analysis was run on a C18 reverse phase column, and individual urushiol congener peaks were assessed by mass spectrometry (MS). Dried poison ivy urushiol was dissolved in ethanol and eluted with a 60 to 100% methanol gradient. Samples were collected and analyzed by MS. Preparative separation of urushiol components of the purified poison ivy extract was performed by reverse phase preparatory FPLC.

EXAMPLE 13

Detoxification of Methylene Chloride Extract—Solvent Removal

Urushiol extract prepared using methylene chloride as the primary solvent was transferred into a round bottom flask and stripped of solvent using a rotary evaporator to near dryness. A sample taken therefrom for GCMS analysis, which indicated the presence of hexane and methylene chloride in the sample. The extract was thrice resuspended in approximately 150 milliliters of diethyl ether and stripped of solvent. Following resuspension in ethanol, the product contained no detectable amount of hexane or methylene chloride.

EXAMPLE 14

Degradation Study for Clinical Solution Stability

A total of six samples (0.5 milliliter each) of urushiol preparations made as described herein using methylene chloride as the primary solvent. Sample concentrations were 50 milligrams per milliliter, 5 milligrams per milliliter, and 0.5 milligram per milliliter, and these samples were prepared in duplicate. One duplicate of each of the three samples was stored at 23 degrees Celsius and the other was stored at 3 degrees Celsius. Gas chromatography profiles were obtained periodically over the course of 249 days to monitor urushiol levels in the samples.

EXAMPLE 15

Gas Chromatography-Mass Spectrometric Analysis of Urushiol

Purified urushiol reconstituted into ethanol was subjected to gas chromatography followed by the determination of mass charge ratio on a Agilent Model 5973N GC-MS System with column C8 reverse column.

EXAMPLE 16

Liquid Chromatographic Analysis of Urushiol

High Pressure Liquid Chromatography (HPLC) analysis was run on C18 reversed phase column, to determine individual urushiol congener peaks by mass spectrometry on a Agilent Model 1100 LC-MS System. Dried poison ivy urushiol was dissolved in ethanol and eluted with a 60 to 100% methanol gradient. Samples were collected and analyzed by ion-trap mass spectrometry.

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A method for extracting urushiol from a plant, the method comprising contacting the plant and a primary organic solvent that is more polar than ethanol for a period of time and thereafter separating the plant from the primary solvent to yield a liquid initial extract; removing the primary solvent from the initial extract to yield a crude extract; extracting the crude extract with a mixture of first and second solvents, the first and second solvents being immiscible and the first solvent being more polar than the second solvent; and recovering urushiol from the first solvent.

2. The method of claim 1, wherein the primary organic solvent is selected from the group consisting of methylene chloride, isopropanol, tetrahydrofuran, dichloromethane, acetonitrile, dimethoxyethane, propanol, chloroform, and pentane and combinations thereof.

3. The method of claim 1, wherein the primary organic solvent is selected from the group consisting of methylene chloride, chloroform, and pentane.

4. The method of claim 1, wherein the first solvent is no more polar than chloroform.

5. The method of claim 1, wherein the first solvent is selected from the group consisting of acetonitrile and chloroform.

6. The method of claim 1, wherein the second solvent is more polar than chloroform.

7. The method of claim 1, wherein the second solvent is selected from the group consisting of alkanes having at least five carbon atoms.

8. The method of claim 1, wherein the second solvent is selected from the group consisting of pentanes, hexanes, and heptanes.

9. The method of claim 1, wherein the plant is selected from the group consisting of cashews, pistachios, mangos, poison ivies, poison oaks, sumacs, smoke trees, marulas, yellow mombins, cuachalalates, lac trees, rengus trees, Burmese lacquer trees, India marking nut trees, ginkgo trees, and combination of these.

10. The method of claim 1, wherein the plant is one of poison ivy and poison oak.

11. The method of claim 1, wherein the primary organic solvent is contacted with leaves of the plant.

12. The method of claim 1, wherein the plant is shredded.

13. The method of claim 1, wherein each step is performed at a temperature not greater than 30 degrees Celsius.

14. The method according to claim 1, further comprising fractionating urushiol recovered from the first solvent using a thiazole-derivatized chromatography medium.

15. The method of claim 14, wherein the medium is a silica gel.

* * * * *